US012307537B2

(12) United States Patent
Guillama et al.

(10) Patent No.: US 12,307,537 B2
(45) Date of Patent: *May 20, 2025

(54) SYSTEM AND METHOD FOR MAKING PATIENT RECORDS FOLLOW A PHYSICIAN

(71) Applicant: The Quantum Group, Inc., Greenacres, FL (US)

(72) Inventors: Noel J. Guillama, Wellington, FL (US); Pedro Martinez, Boca Raton, FL (US)

(73) Assignees: The Quantum Group, Inc., Lake Worth, FL (US); Noel Guillama, Wellington, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/047,394

(22) Filed: Oct. 18, 2022

(65) Prior Publication Data

US 2023/0053719 A1 Feb. 23, 2023

Related U.S. Application Data

(63) Continuation of application No. 17/028,249, filed on Sep. 22, 2020, now Pat. No. 11,501,393, which is a (Continued)

(51) Int. Cl.
 *G06Q 50/22* (2024.01)
 *G16H 10/60* (2018.01)
 *G16H 40/20* (2018.01)

(52) U.S. Cl.
 CPC .......... *G06Q 50/22* (2013.01); *G16H 10/60* (2018.01); *G16H 40/20* (2018.01)

(58) Field of Classification Search
 CPC ......... G06Q 50/22; G16H 10/60; G16H 40/20
 (Continued)

(56) References Cited

U.S. PATENT DOCUMENTS 5,541,583 A 7/1996 Mandelbaum
5,671,445 A 9/1997 Gluyas
(Continued)

OTHER PUBLICATIONS

Whiting, Rick; A Prescription for Privacy—The Palo Alto Medical Foundation is providing patients with secure online access to their medical records; InformationWeek : 49. United Business Media LLC. (Jun. 18, 2001) (Year: 2001).*

(Continued)

*Primary Examiner* — Hiep V Nguyen
(74) *Attorney, Agent, or Firm* — Nixon Peabody LLP

(57) ABSTRACT

A computer-based system for providing physicians automatic, secure access to patient records at the time a patient visits and consults a physician. The system can include one or more computing devices configured to process and display data. The system can also include one or more emitting devices carried by physicians for identifying each particular physician and one or more scanning devices configured to detect and communicatively link to the one or more emitting devices based on the proximity of the physician to an examination room. Additionally, the system can include a manager module communicatively linked to the one or more scanning devices and configured to manage the signal data from the one or more scanning devices. Furthermore, the system can also include one or more servers communicatively linked with the one or more computing devices, one or more scanning devices, and manager module, the one or more servers configured to authenticate and register a particular patient upon a visit to a hospital or office, synchronize the particular physician identifier, patient identifier, personal wellness electronic record (PWER), and examination room identifier based upon physician's proximity to an examination room, initiate a physician-patient session at the at least one computing device at the examination room, transfer the PWER to the at least one computing device at the exami- (Continued)

nation room, and automatically terminate the physician-patient session and receive the PWER based upon the physician leaving the proximity of the examination room.

20 Claims, 2 Drawing Sheets

Related U.S. Application Data continuation of application No. 12/472,185, filed on May 26, 2009, now Pat. No. 10,817,964.

(60) Provisional application No. 61/057,104, filed on May 29, 2008.

(58) Field of Classification Search
USPC .............................................................. 705/3
See application file for complete search history.

(56) References Cited

U.S. PATENT DOCUMENTS

| | | | |
|---|---|---|---|
| 6,040,786 A | 3/2000 | Fujioka | |
| 6,325,285 B1 | 12/2001 | Baratelli | |
| 6,347,329 B1 | 2/2002 | Evans | |
| 7,289,825 B2 | 10/2007 | Fors | |
| 7,598,853 B2 | 10/2009 | Becker | |
| 2002/0010679 A1* | 1/2002 | Felsher | G06F 21/6245 |
| | | | 705/51 |
| 2002/0161795 A1 | 10/2002 | O'Rourke | |
| 2003/0088441 A1 | 5/2003 | McNerney | |
| 2004/0111298 A1 | 6/2004 | Schoenberg | |
| 2005/0005136 A1 | 1/2005 | Chen | |
| 2005/0114150 A1 | 5/2005 | Franklin | |
| 2005/0139656 A1 | 6/2005 | Arnouse | |
| 2005/0149358 A1 | 7/2005 | Sacco | |
| 2005/0182661 A1 | 8/2005 | Allard | |
| 2005/0187792 A1 | 8/2005 | Harper | |
| 2005/0201345 A1 | 9/2005 | Williamson | |
| 2005/0216313 A1 | 9/2005 | Claud | |
| 2006/0006999 A1 | 1/2006 | Walczyk | |
| 2006/0074713 A1 | 4/2006 | Conry | |
| 2006/0143041 A1* | 6/2006 | Tipirneni | G06Q 10/10 |
| | | | 715/733 |
| 2006/0183426 A1* | 8/2006 | Graves | H04W 52/241 |
| | | | 455/63.1 |
| 2006/0185005 A1 | 8/2006 | Graves | |
| 2006/0229909 A1 | 10/2006 | Kaila | |
| 2006/0288095 A1 | 12/2006 | Torok | |
| 2007/0005403 A1 | 1/2007 | Kennedy | |
| 2007/0019845 A1 | 1/2007 | Kato | |
| 2007/0033072 A1 | 2/2007 | Bildirici | |
| 2007/0132586 A1 | 6/2007 | Plocher | |
| 2007/0158411 A1 | 7/2007 | Krieg, Jr. | |
| 2007/0194939 A1 | 8/2007 | Alvarez | |
| 2007/0258626 A1 | 11/2007 | Reiner | |
| 2007/0279187 A1 | 12/2007 | Hekmatpour | |
| 2008/0071577 A1 | 3/2008 | Highley | |
| 2008/0129450 A1 | 6/2008 | Riegebauer | |
| 2008/0180213 A1 | 7/2008 | Flax | |
| 2008/0228524 A1 | 9/2008 | Brown | |
| 2008/0251579 A1 | 10/2008 | Larsen | |
| 2008/0316045 A1 | 12/2008 | Sriharto | |
| 2009/0057399 A1* | 3/2009 | Sajkowsky | G07F 7/00 |
| | | | 235/380 |
| 2009/0076849 A1 | 3/2009 | Diller | |
| 2009/0206992 A1* | 8/2009 | Giobbi | G16H 10/60 |
| | | | 340/5.82 |
| 2009/0281825 A1 | 11/2009 | Larsen | |
| 2009/0296540 A1 | 12/2009 | Gilbert | |
| 2010/0071044 A1 | 3/2010 | Khan | |
| 2012/0323607 A1 | 12/2012 | Jin | |

OTHER PUBLICATIONS

Carryl Clyde; Universal Physical Access Control System (UPACS); Florida Atlantic University; ProQuest Dissertations Publishing, 2015. 10095867 (Year: 2015).

Fry et al., "MASCAL: RFID Tracking of Patients, Staff, and Equipment to Enhance Hospital Response to Mass Casualty Events," National Institutes of Health, 2005 (7 pages).

PCT International Search Report and Opinion, dated Jul. 2, 2009.

\* cited by examiner

SYSTEM AND METHOD FOR MAKING PATIENT RECORDS FOLLOW A PHYSICIAN

CROSS-REFERENCE TO RELATED APPLICATIONS

This application is a continuation of U.S. application Ser. No. 17/028,249, filed on Sep. 22, 2020, now allowed, which is a continuation of U.S. application Ser. No. 15/333,728, filed on Oct. 25, 2016, now granted as U.S. Pat. No. 10,954,413, which is a continuation of U.S. application Ser. No. 12/472,185, filed on May 26, 2009, now granted as U.S. Pat. No. 10,817,964, which claims the benefit of U.S. Provisional Patent Application No. 61/057,104, filed on May 29, 2008, each of which is hereby incorporated by reference herein in its entirety.

FIELD OF THE INVENTION

The present invention is related to the fields of data retrieval, processing, and display, and more particularly, to computer-based systems and methods for providing automatic, secure access to patient records.

BACKGROUND OF THE INVENTION

Today, a significant challenge physicians have to deal with is having to rely on patient records, that are largely in paper form, when consulting with patients. Often times, such patient records can be incomplete, tough to analyze in an efficient manner, and burdensome. Even if patient records are stored in electronic form, it still remains a challenge to provide immediate, automatic, and secure access to a particular patient's record, especially at the time the patient is visiting the physician. The inability to provide such access to patient records has led to problems and inefficiencies such as delayed patient consultations, delayed treatments, increased costs, and unnecessary expenditures in labor. By relying on the current methods for accessing records, physicians face a greater probability of receiving inaccurate and incomplete records. This, in turn, ultimately leads to a greater probability of making inaccurate medical diagnoses. These inefficiencies are further amplified as a physician consults with more and more patients.

As a result, there is a need for more effective and efficient means providing physicians with direct, automatic, and secure access to patient records. Furthermore, there is a need for effective and efficient systems and methods to enable automatic, secure access to patient records, especially when a patient visits a particular physician.

SUMMARY OF THE INVENTION

The present invention is directed to systems and methods for providing automatic, secure access to patient records, particularly when a physician enters an examination room to treat and/or consult a patient.

One embodiment of the invention is a computer-based system for providing physicians with automatic, secure access to patient records at the time a patient visits and consults a physician. The system can include one or more computing devices configured to process and display data. The system can also include one or more emitting devices carried by physicians for identifying each particular physician and one or more scanning devices configured to detect and communicatively link to the one or more emitting devices based on the proximity of the physician to an examination room. Additionally, the system can include a manager module communicatively linked to the one or more scanning devices and configured to manage the signal data from the one or more scanning devices. Furthermore, the system can also include one or more servers communicatively linked with the one or more computing devices, one or more scanning devices, and the manager module. The one or more servers can be configured to authenticate and register a particular patient upon a visit to a hospital or office, synchronize the particular physician identifier, patient identifier, personal wellness electronic record (PWER), and examination room identifier based upon the physician's proximity to an examination room, initiate a physician-patient session at the one or more computing devices at the examination room, transfer the PWER to the one or more computing devices at the examination room, and automatically terminate the physician-patient session and receive the PWER based upon the physician leaving the proximity of the examination room.

Another embodiment of the invention is a computer-based method for providing physicians automatic, secure access to patient records at the time a patient visits and consults the physician. The method can include authenticating and registering a particular patient upon a visit to a hospital or office. The method can also include synchronizing a particular physician identifier, patient identifier, personal wellness electronic record (PWER), and examination room identifier based upon physician's proximity to an examination room. Additionally, the method can further include initiating a physician-patient session at a computer system at the examination room and transferring the PWER from one or more servers to the computer system at the examination room. Moreover, the method can also include automatically terminating the physician-patient session and transferring the PWER to the one or more servers based upon the physician leaving the proximity of the examination room.

Yet another embodiment of the invention is a computer-readable medium which contains computer-readable code that when loaded on a computer causes the computer to authenticate and register a particular patient upon a visit to a hospital or office, to synchronize a particular physician, patient, personal wellness electronic record (PWER), and examination room based upon physician's proximity to the examination room, to initiate a physician-patient session at a computer system at the examination room, to transfer the PWER from one or more servers to the computer system at the examination room; and to automatically terminate the physician-patient session and transfer the PWER to the one ore more servers based upon the physician leaving the proximity of the examination room.

BRIEF DESCRIPTION OF THE DRAWINGS

There are shown in the drawings, embodiments which are presently preferred. It is expressly noted, however, that the invention is not limited to the precise arrangements and instrumentalities shown.

DETAILED DESCRIPTION

Figure 1:
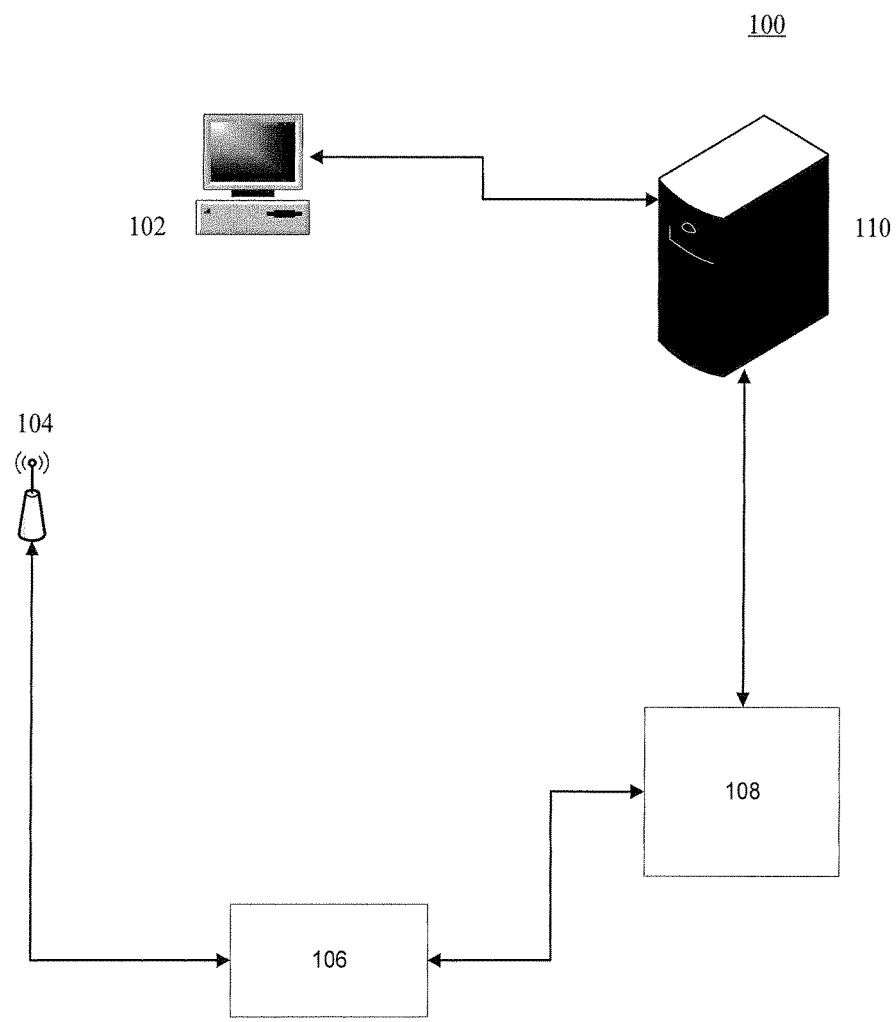
FIG. 1 is a schematic view of a system for providing physicians automatic, secure access to patient records at the time a patient visits and consults a physician, according to one embodiment of the invention.

Referring initially to FIG. 1, a system 100 for providing physicians automatic, secure access to patient records at the time a patient visits and consults a physician, according to one embodiment of the invention, is schematically illustrated. The system includes one or more computing devices 102 configured to process and display data 102. For example, the computing devices 102 can be desktop computers, laptops, personal digital assistants, or other similar computing devices. The system 100 further includes one or more emitting devices 104 carried by the physicians for identifying each particular physician. Additionally, the system 100 includes one or more scanning devices 106 configured to detect and communicatively link to the one or more emitting devices 104 based on the proximity of the physician to an examination room.

The system 100 can also include a manager module 108 that is communicatively linked to the one or more scanning devices 106 and configured to manage the signal data coming from the one or more scanning devices 106. Furthermore, the system 100 can include one or more servers 110 communicatively linked with the one or more computing devices 102, one or more scanning devices 106, and manager module 108. Alternatively, the manager module 108 can be implemented in hardwired, dedicated circuitry for performing the operative functions described herein. In another embodiment, the manager module 108 can be implemented in computer-readable code configured to execute on a particular computing machine. In yet another embodiment, however, the manager module 108 can be implemented in a combination of hardwired circuitry and computer-readable code.

Operatively, when a physician enters a patient examination room, the one or more emitting devices 104 carried by the physician send a physician identifier to the one or more scanning devices 106. The one or more scanning devices 106 relay the physician identifier and examination room identifier to the manager module 108 and the manager module 108 transfers the signal to the one or more servers 110 for processing. The one or more servers 110 are configured to authenticate and register a particular patient upon a visit to a hospital or office, which results in the creation of a patient identifier, synchronize the particular physician identifier, patient identifier, personal wellness electronic record (PWER), and examination room identifier based upon physician's proximity to an examination room, initiate a physician-patient session at the one or more computing devices 102 at the examination room, transfer the PWER to the one or more computing devices 102 at the examination room, and automatically terminate the physician-patient session and receive the PWER based upon the physician leaving the proximity of the examination room. Even though one computing device 102, one emitting device 104, one scanning device 106, and one server 110 are shown, it will be apparent to one of ordinary skill that a greater number of computing devices, emitting devices, scanning devices, and servers can be utilized in the system 100.

According to a particular embodiment, the one or more computing devices 102 can be configured to electronically update the PWER during or after the examination. The one or more emitting devices 104 can be, for example, radio frequency identification chips, cards, or other emitting devices carried by the physician. The scanning devices 106 of the system 100 can be radio frequency identification readers that are utilized to detect the one or more emitting devices 104, for example. In another embodiment, the manager module 108 can be configured to alert the one or more servers 110 of the presence of the physician in the examination room.

In yet another embodiment, the one or more servers 110 can be configured to preload the PWER into an electronic data buffer for transmission. For example, when a patient visits a particular physician, the patient is registered and authenticated by the system 100. The system 100 creates a patient identifier and the PWER for that patient can then be preloaded in the system 100 to enable fast and efficient access to the records. Additionally, the one or more servers 110 can be configured to provide at least one of a privacy restriction and a security restriction for the accessing of the PWER. For example, based on the particular patient and/or policies pertaining to the patient, the one or more servers 110 can ensure the right level of access and security measures for a particular PWER. According to still another embodiment, the one or more servers 110 can be configured to reinitiate a physician-patient session when the physician enters another examination room or re-enters the original examination room.

Figure 2:
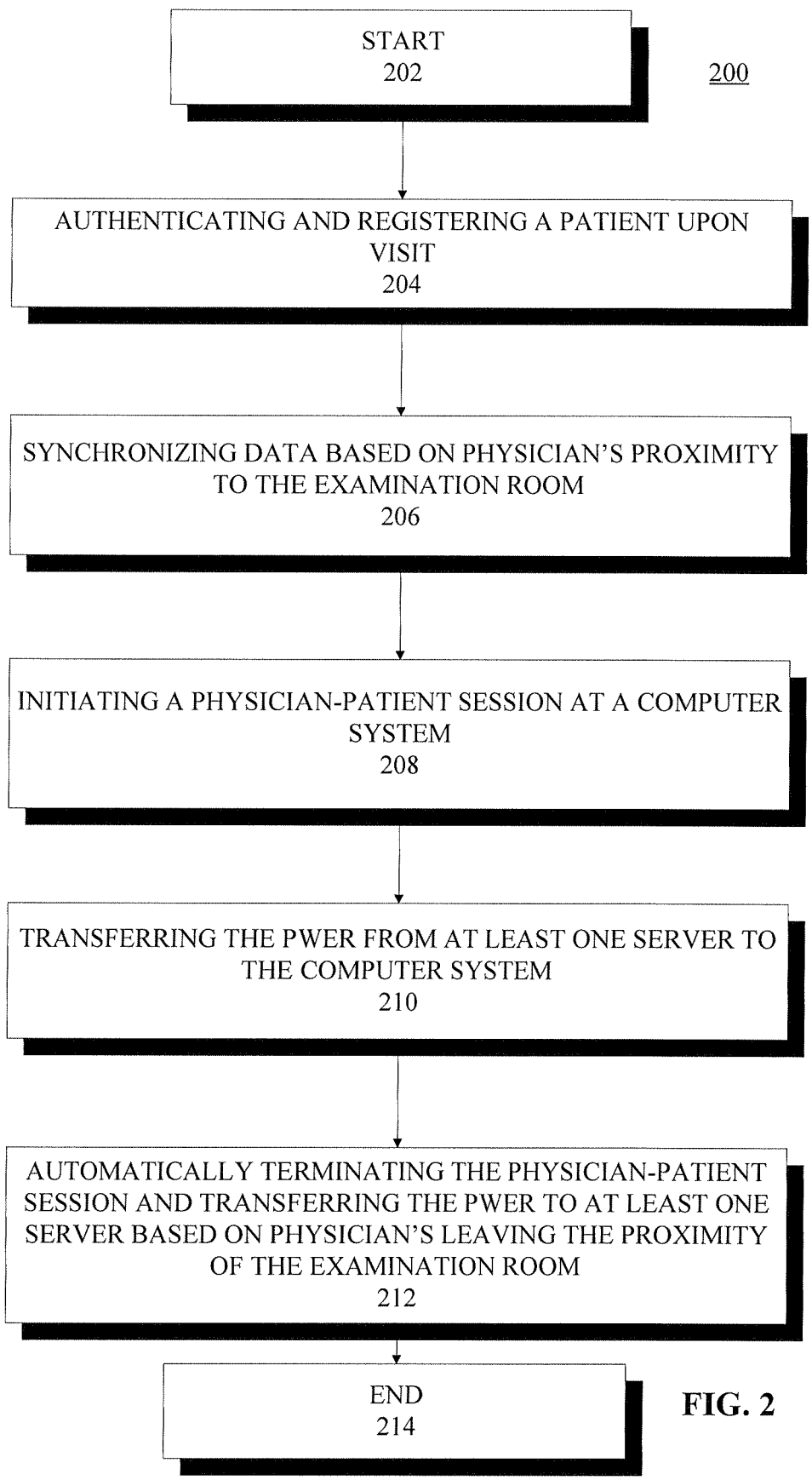
FIG. 2 is a flowchart of steps in a method for providing physicians automatic, secure access to patient records at the time a patient visits and consults the physician, according to another embodiment of the invention.

Referring now to FIG. 2, a flowchart is provided that illustrates certain method aspects of the invention. The flowchart depicts steps of a method 200 for providing physicians with automatic, secure access to patient records at the time a patient visits and consults the physician. The method 200 illustratively includes, after the start step 202, authenticating and registering a particular patient upon a visit to a hospital or office at step 204. The method 200 also includes synchronizing a particular physician identifier, patient identifier, personal wellness electronic record (PWER), and examination room identifier based upon physician's proximity to an examination room at step 206. Additionally, the method 200 includes at step 208 initiating a physician-patient session at a computer system at the examination room. The method 200 also includes transferring the PWER from one or more servers to the computer system at the examination room at step 210. The method 200 further includes at step 212 automatically terminating the physician-patient session and transferring the PWER to the one or more servers based upon the physician leaving the proximity of the examination room. The method 200 illustratively concludes at step 214.

The method 200 can also include preloading the PWER into an electronic data buffer for transmission. For example, when a patient visits a hospital or office, the PWER for the patient can be preloaded into a computer system. This will enable prompt display when the physician comes to treat and/or consult the patient.

According to another embodiment, the method 200 can further include, at the synchronizing step 206, using a scanning device, for detecting an emitting device carried by the physician. The emitting device can contain identification information for a particular physician. In one embodiment, the scanning device can be a radio frequency identification reader that detects a radio frequency identification chip, card, or other emitting device carried by the physician. Moreover, the synchronizing step 206 also can include communicating with a manager module, where the manager module alerts the one or more servers of the presence of the physician in the examination room.

According to yet another embodiment, the method 200 can include providing at least one of a privacy restriction and a security restriction for the accessing of the PWER. The method 200 can also include electronically updating the PWER during or after an examination. In another embodiment, the method 200 can further include reinitiating a physician-patient session when the physician enters another examination room or re-enters the original examination room.

The invention can be realized in hardware, software, or a combination of hardware and software. The invention can be realized in a centralized fashion in one computer system, or in a distributed fashion where different elements are spread across several interconnected computer systems. Any type of computer system or other apparatus adapted for carrying out the methods described herein is suitable. A typical combination of hardware and software can be a general purpose computer system with a computer program that, when being loaded and executed, controls the computer system such that it carries out the methods described herein.

The invention, as already mentioned, can be embedded in a computer program product, such as magnetic tape, an optically readable disk, or other computer-readable medium for storing electronic data. The computer program product can comprise computer-readable code, (defining a computer program) which when loaded in a computer or computer system causes the computer or computer system to carry out the different methods described herein. Computer program in the present context means any expression, in any language, code or notation, of a set of instructions intended to cause a system having an information processing capability to perform a particular function either directly or after either or both of the following: a) conversion to another language, code or notation; b) reproduction in a different material form.

The preceding description of preferred embodiments of the invention have been presented for the purposes of illustration. The description provided is not intended to limit the invention to the particular forms disclosed or described. Modifications and variations will be readily apparent from the preceding description. As a result, it is intended that the scope of the invention not be limited by the detailed description provided herein.

We claim:

1. A server system for providing automatic and secure access to electronic patient records, the server system being communicatively coupled to a computing device associated with an examination room and an examination room identifier, the server system comprising:
   one or more processors; and
   a memory storing machine readable instructions configured to cause the one or more processors to:
      receive an indication that a patient is registered and authenticated to be treated in the examination room associated with the examination room identifier;
      responsive to receiving the indication that a patient is registered and authenticated, create a patient identifier associated with the patient;
      preload a personal wellness electronic record (PWER) in an electronic data buffer of the server system for transmission;
      determine, based on a first signal from a physician emitting device associated with a physician identifier transferred to the server system for processing by the server system, that the physician emitting device is within the examination room associated with the examination room identifier;
      identify, based on the examination room identifier, the computing device, wherein the computing device is located in the examination room associated with the examination room identifier; and
      responsive to determining that the physician emitting device is within the examination room associated with the examination room identifier:
         synchronize the patient identifier, the physician identifier, the examination room identifier, and the PWER associated with the patient; and
         cause the PWER to automatically transfer from the electronic data buffer of the server system to the computing device that is located in the examination room.

2. The server system of claim 1, wherein the machine-readable instructions are further configured to cause the one or more processors to provide at least one restriction requirement for accessing the PWER.

3. The server system of claim 2, wherein the at least one restriction requirement comprises at least one of a privacy restriction and a security restriction.

4. The server system of claim 2, wherein the machine-readable instructions are further configured to cause the one or more processors to determine that the physician identifier satisfies the at least one restriction requirement.

5. The server system of claim 1, wherein the machine-readable instructions are further configured to cause the one or more processors to:
   prior to automatically transferring the PWER from the electronic data buffer of the server system, initiate a physician-patient session on the computing device that is located in the examination room.

6. The server system of claim 5, wherein the machine-readable instructions are further configured to cause the one or more processors to:
   determine, based on a second signal from the physician emitting device, the second signal transferred to the server system for processing by the server system, that the physician emitting device has left the examination room associated with the examination room identifier; and
   responsive to determining that the physician emitting device has left the examination room associated with the examination room identifier, cause the physician-patient session to automatically terminate.

7. The server system of claim 6, wherein the machine-readable instructions are further configured to cause the one or more processors to:
   responsive to determining that the physician emitting device has left the examination room associated with the examination room identifier, cause the PWER to transfer from the computing device to the server system.

8. The server system of claim 5, wherein the machine-readable instructions are further configured to cause the one or more processors to:
   determine, based on a second signal from the physician emitting device, the second signal transferred to the server system for processing by the server system, that the physician emitting device is in the examination room associated with the examination room identifier; and
   responsive to determining that the physician emitting device is in the examination room associated with the examination room identifier, cause the PWER to automatically update.

9. A computer-based method for providing secure access to electronic patient records via a server system, the server system being communicatively coupled to a computing device associated with an examination room and an examination room identifier, the method comprising:

receiving, at the server system, an indication that a patient is registered and authenticated to be treated in the examination room associated with the examination room identifier;

responsive to receiving the indication that a patient is registered and authenticated, creating, by the server system, a patient identifier associated with the patient;

preloading, by the server system, a personal wellness electronic record (PWER) in an electronic data buffer of the server system for transmission;

determining, based on a first signal from a physician emitting device associated with a physician identifier transferred to the server system for processing by the server system, that the physician emitting device is within the examination room associated with the examination room identifier;

identifying, based on the examination room identifier, the computing device, wherein the computing device is located in the examination room associated with the examination room identifier; and responsive to determining that the physician emitting device is within the examination room associated with the examination room identifier:

synchronizing, by the server system, the patient identifier, the physician identifier, the examination room identifier, and the PWER associated with the patient; and causing, by the server system, the PWER to automatically transfer from the electronic data buffer of the server system to the computing device that is located in the examination room.

10. The method of claim 9, further comprising providing, by the server system, at least one restriction requirement for accessing the PWER.

11. The method of claim 10, wherein the at least one restriction requirement comprises at least one of a privacy restriction and a security restriction.

12. The method of claim 10, further comprising determining, by the server system, that the physician identifier satisfies the at least one restriction requirement.

13. The method of claim 9, further comprising:

prior to automatically transferring the PWER from the electronic data buffer of the server system, initiate, by the server system, a physician-patient session on the computing device that is located in the examination room.

14. The method of claim 13, further comprising:

determining, based on a second signal from the physician emitting device, the second signal transferred to the server system for processing by the server system, that the physician emitting device has left the examination room associated with the examination room identifier; and responsive to determining that the physician emitting device has left the examination room associated with the examination room identifier, causing, by the server system, the physician-patient session to automatically terminate.

15. The method of claim 14, further comprising:

responsive to determining that the physician emitting device has left the examination room associated with the examination room identifier, causing, by the server system, the PWER to transfer from the computing device to the server system.

16. The method of claim 13, further comprising:

determining, based on a second signal from the physician emitting device, the second signal transferred to the server system for processing by the server system, that the physician emitting device is in the examination room associated with the examination room identifier; and responsive to determining that the physician emitting device is in the examination room associated with the examination room identifier, causing, by the server system, the PWER to automatically update.

17. A non-transitory computer-readable storage medium having stored therein computer-readable instructions, which, when loaded in and executed by one or more processors of a server system, causes the server system to:

receive an indication that a patient is registered and authenticated to be treated in an examination room associated with an examination room identifier;

responsive to receiving the indication that a patient is registered and authenticated, create a patient identifier associated with the patient;

preload a personal wellness electronic record (PWER) in an electronic data buffer of a server system for transmission;

determine, based on a first signal from a physician emitting device associated with a physician identifier transferred to server system for processing by the server system, that the physician emitting device is within the examination room associated with the examination room identifier;

identify, based on the examination room identifier, the computing device, wherein the computing device is located in the examination room associated with the examination room identifier; and responsive to determining that the physician emitting device is within the examination room associated with the examination room identifier:

synchronize the patient identifier, the physician identifier, the examination room identifier, and the PWER associated with the patient; and cause the PWER to automatically transfer from the electronic data buffer of the server system to the computing device that is located in the examination room.

18. The non-transitory computer-readable storage medium of claim 17, wherein the computer-readable instructions, which, when loaded in and executed by the one or more processors of the server system, further cause the server system to provide at least one restriction requirement for accessing the PWER.

19. The non-transitory computer-readable storage medium of claim 17, wherein the computer-readable instructions, which, when loaded in and executed by the one or more processors of the server system, further cause the server system to:

prior to automatically transferring the PWER from the electronic data buffer of the server system, initiate a physician-patient session on the computing that is located in the examination room.

20. The non-transitory computer-readable storage medium of claim 19, wherein the computer-readable instructions, which, when loaded in and executed by the one or more processors of the server system, further cause the server system to:

determine, based on a second signal from the physician emitting device, the second signal transferred to the server system for processing by the server system, that the physician emitting device has left the examination room associated with the examination room identifier; and responsive to determining that the physician emitting device has left the examination room associated with the examination room identifier, cause the physician-patient session to automatically terminate.

\* \* \* \* \*